United States Patent [19]

Fukumoto

[11] Patent Number: 4,624,834
[45] Date of Patent: Nov. 25, 1986

[54] DEVICE FOR MEASURING THE ABSOLUTE VALUE OF THE DENSITY OF SALTS IN ATMOSPHERE

[75] Inventor: Takaaki Fukumoto, Kishiwada, Japan

[73] Assignee: Mitsubishi Denki Kabushiki Kaisha, Tokyo, Japan

[21] Appl. No.: 686,848

[22] Filed: Dec. 26, 1984

[30] Foreign Application Priority Data

Dec. 27, 1983 [JP] Japan ................................. 58-246893
Jan. 6, 1984 [JP] Japan ..................................... 59-1051

[51] Int. Cl.$^4$ ............................................. B01K 3/02
[52] U.S. Cl. ........................................ 422/90; 422/91; 422/92
[58] Field of Search ........................ 422/88, 90, 91, 92

[56] References Cited

U.S. PATENT DOCUMENTS 3,457,145  7/1969  Jones ..................................... 422/88

*Primary Examiner*—Frank Sever
*Attorney, Agent, or Firm*—Birch, Stewart, Kolasch & Birch

[57] ABSTRACT

A device for measuring the absolute value of the density of salts in the atmosphere including: an airtight water tank containing super pure water, a device for supplying super pure water to the airtight water tank, an elongated cylindrical pipe for bubbling a predetermined quantity of air from the atmosphere into the super pure water of a predetermined quantity, from inside the airtight water tank, an outlet for exhausting the super pure water in the airtight water tank after the bubbling, a sodium ion analyzer for measuring the density of sodium ions in the exhausted super pure water, and a background value measuring device including the sodium ion analyzer for measuring the density of sodium ions in the super pure water at the water supplying means while bubbling. Another device for measuring the absolute value of the density of salts in the atmosphere further includes a device for washing the airtight water tank by super pure water after the exhaustion of the super pure water in the tank. Another measuring device further includes a mesh provided at the bubbling pipe.

12 Claims, 4 Drawing Figures

DEVICE FOR MEASURING THE ABSOLUTE VALUE OF THE DENSITY OF SALTS IN ATMOSPHERE

FIELD OF THE INVENTION

The present invention relates to a device for measuring the absolute value of the density of salts in atmosphere and continuously monitoring the same.

BACKGROUND OF THE INVENTION

FIG. 1 shows a device for measuring the absolute value of the density of salts in atmosphere already invented by the inventor. In the Figure, the reference numeral 7 designates an airtight water tank of a predetermined capacity which contains the super pure water 37 of a predetermined quantity the resistivity of which is above 15MΩcm. The tank 7 is made up of a material from which any dissolved material including sodium ions does not soak out, such as a transparent vinyl chloride. The numeral 3 designates a pipe for supplying the super pure water to the tank 7. The numeral 2 designates a valve provided at the pipe 3. The pipe 3 and the valve 2 constitute a means 30 for supplying the water. The numeral 13 designates a bubbling pipe for bubbling the air in atmosphere into the super pure water 37 in the tank 7 to make the salts in atmosphere dissolved into the super pure water 37. The numerals 8, 9, 10, 11, and 12 designate a pipe, a valve, a pump, a flow meter, and a timer, all of which constitute a means 40 for supplying the air in atmosphere to the bubbling pipe 13. The numerals 14a and 14b designate flow switches to hold the level of the super pure water 37 contained in the tank 7 at predetermined levels. The numeral 4 designates an exhaust pipe for exhausting the super pure water 37 contained in the tank 7 to the outside. The numeral 15 designates a valve provided at the exhaust pipe 4. The exhaust pipe 4 and the valve 15 constitute a means 50 for exhausting the water. The numeral 5 designates a sodium ion analyzer for measuring the density of $Na^+$ ions in the exhausted super pure water of a predetermined quantity. The material taking inlet 5a of the analyzer 5 is sunk in the exhausted water.

The device will be operated as follows:

At first, the valve 2 in the means 30 for supplying the water is opened, and the super pure water 37, the resistivity of which is above 15MΩ cm, is supplied to the airtight water tank 7 through the pipe 3. When the flow switch 14a, operates, the valve 2 in the water supplying means 30 is closed to stop the supply of the super pure water 37 to the tank 7. Thus, the airtight water tank 7 is filled up with the super pure water 37 of a predetermined quantity. When the valve 9 in the means 40 for supplying the air in atmosphere is opened and the pump 8 is operated, the air in atmosphere is sent to the bubbling pipe 13 through the pipe 8 at a constant flow rate for a predetermined time. The bubbling pipe 13 operates to bubble the air into the super pure water 37 in the tank 7 to make the salts, that is, NaCl in the air dissolved into the super pure water 37. When the bubbling is concluded, the valve 9 is closed, the valve 15 in the means 50 for exhausting the water is opened, and the super pure water in the tank 7 is exhausted to the outside through the pipe 4 at a constant flow rate caused by its positional potential. The sodium ion analyzer 5 with its material taking inlet 5a sunk in the exhausted super pure water operates to measure the density of $Na^+$ ions in the super pure water. Then, the absolute value of the density of salts in atmosphere is obtained from the density of $Na^+$ ions in the super pure water measured by the sodium ion analyzer 5 by executing an operation including the mass-conversion between $Na^+$ and NaCl.

Caused by the exhaustion of the super pure water, the flow switch 14b operates to open the valve 2, and thereafter, the above mentioned measuring operation is repeated. This enables continuous monitoring. In this case, the quantity of the air to be supplied is measured by the flow meter 11 and is regulated by the valve 9. The time period during which the air is supplied can be regulated by the timer 12. Furthermore, the time period during which the super pure water is supplied can be regulated by a means (not shown) provided in the water supplying means 30.

In this device for measuring the absolute value of the density of salts in atmosphere under such construction, however, the background value of the sodium ion analyzer 5, that is, the density of $Na^+$ ions included in the super pure water 37 before dissolving the air therein is not stable while bubbling. Furthermore, the water tank 7 is not washed while continuously monitoring, and accordingly, the reliability of the measured result is diminished and is influenced by the remaining sodium ions in the water tank 7.

OBJECTS AND SUMMARY OF THE INVENTION

The present invention is directed to solve the problems pointed out above, and has for its object to provide a device for measuring the absolute value of the density of salts in atmosphere and continuously monitoring the same while being capable of obtaining a highly reliable result.

Another object of the present invention is to provide a device for measuring the absolute value of the density of salts in atmosphere where bubbles are further minimized, thereby obtaining a more reliable result.

Other objects and advantages of the present invention will become apparent from the detailed description given hereinafter; it should be understood, however, that the detailed description and specific embodiment are given by way of illustration only, since various changes and modifications within the spirit and scope of the invention will become apparent to those skilled in the art from this detailed description.

According to one aspect of the present invention, a device for measuring the absolute value of the density of salts in atmosphere is provided with a background value measuring means for measuring the density of sodium ions in the super pure water at the water supplying means while bubbling, and further a means for washing the airtight water tank by super pure water after the exhaustion of the super pure water.

According to another aspect of the present invention, a device for measuring the absolute value of the density of salts in atmosphere is provided with a mesh at the bubbling means.

DETAILED DESCRIPTION OF THE PREFERRED EMBODIMENTS

Figure 2:
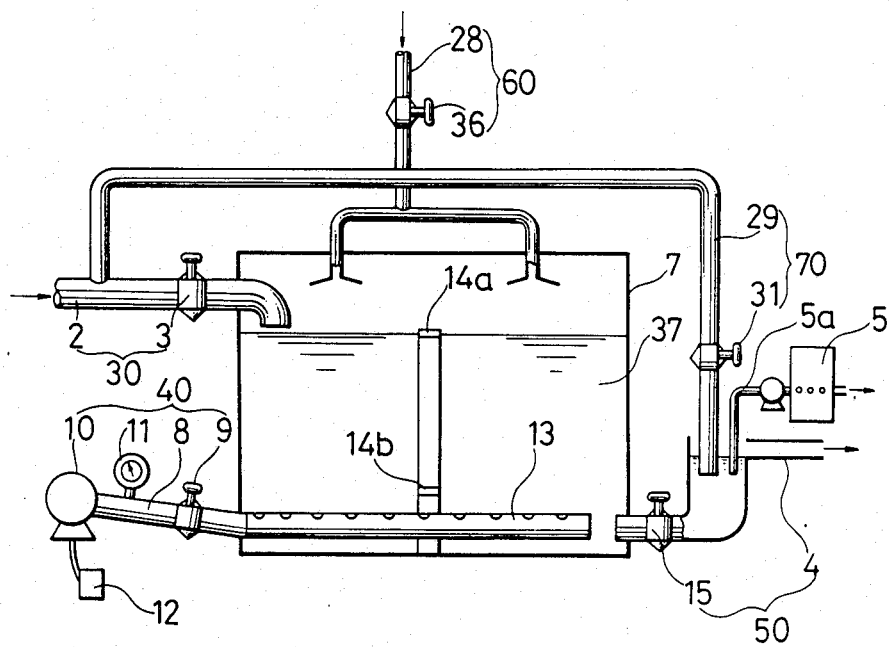
FIG. 2 is a schematic diagram showing a device for measuring the absolute value of the density of salts in atmosphere as a first embodiment of the present invention.

Reference will now be particularly made to FIG. 2 which shows a first embodiment of the present invention.

Figure 1:
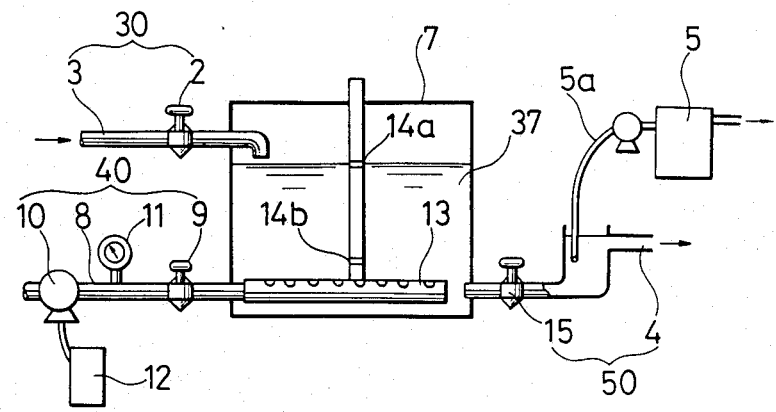
FIG. 1 is a schematic diagram showing a prior art device for measuring the absolute value of the density of salts in atmosphere.

In the Figure, the same reference numerals are used to designate the same or corresponding elements as those in FIG. 1. The reference numeral 29 designates a bypass pipe for supplying super pure water at the water supplying means 30 to the material taking inlet 5a of the sodium ion analyzer 5 while bubbling through bypass. This the bypass pipe 29 is located upstream of the water flow from the water tank 7 to the exhaust pipe 4 relative to the material taking inlet 5a. The numeral 31 designates a valve provided at the pipe 29. The pipe 29 and the valve 31 constitute a bypass means 70 for supplying super pure water therethrough, wherein the bypass means 70 and the sodium ion analyzer 5 constitute a background value measuring means for measuring the density of sodium ions in the super pure water at the water supplying means 30 while bubbling. The reference numeral 28 designates a pipe for supplying super pure water for washing the water tank 7, and the numeral 36 designates a valve provided at the pipe 28. The pipe 28 and the valve 36 constitute a means 60 for washing the water tank 7.

The device will be operated as follows:

The super pure water 37 is supplied from the water supplying means 30 to the airtight water tank 7, and the water tank 7 is filled with the super pure water 37 up to the level of the upper flow switch 14a. Thereafter, the air in atmosphere is supplied to the bubbling pipe 13 by the air supplying means 40 at a predetermined flow rate for a predetermined time, and the air is bubbled into the super pure water 37 by the bubbling pipe 13. After the bubbling is concluded, the super pure water 37 is exhausted to the outside by the exhausting means 50. The exhausted super pure water is led to the sodium ion analyzer 5 through its material taking inlet 5a, and the density of Na+ ions are measured thereby.

In the bubbling operation, the super pure water is supplied from the water supplying means 30 to the material taking inlet 5a of the sodium ion analyzer 5 at a predetermined flow rate by a bypass means 70 for supplying super pure water therethrough, whereby the background value of the sodium ions, that is, the density of sodium ions in the super pure water before bubbling is measured by the sodium ion analyzer 5. After the super pure water to which the air is bubbled is exhausted, super pure water is supplied to the water tank 7 from above the tank 7 by the pipe 28 which is branched into two pipes inside the water tank 7, and the water tank 7 is washed thereby. By repeating the above-described operation, it is possible to measure and continuously monitor the absolute value of the salts in atmosphere at a stable background value of sodium ions, achieving a highly reliable result.

According to the device of FIG. 2, a bypass means for supplying the super pure water to the sodium ion analyzer through the bypass means is provided so as to stabilize the background value of the sodium ion analyzer, and a means for washing the water tank using the super pure water is provided so as to remove the remaining sodium ions in the tank. Such construction can provide a highly reliable result.

Figure 3:
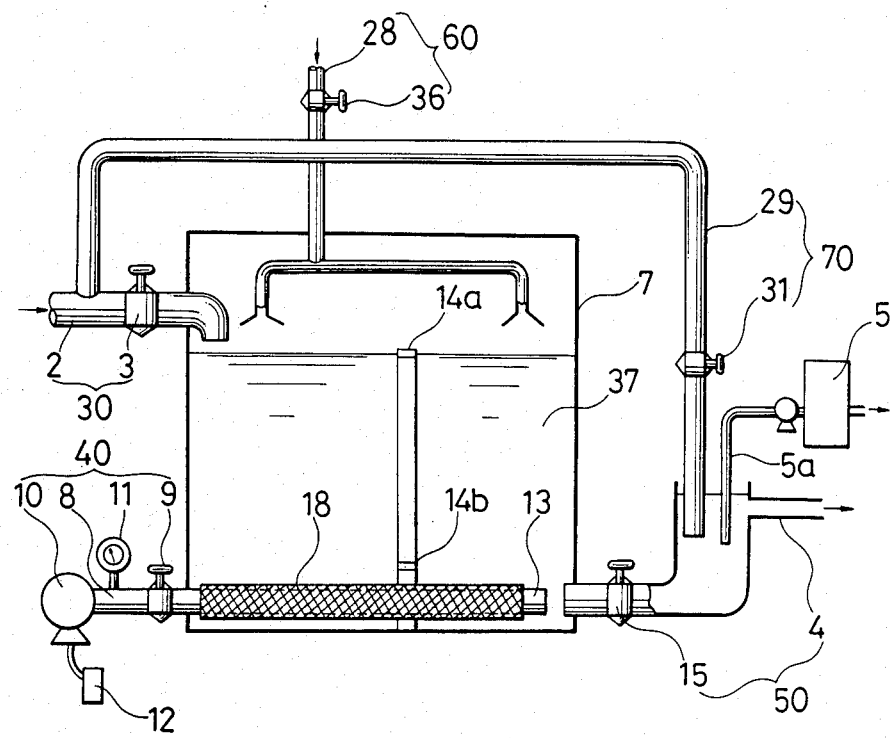
FIG. 3 is a schematic diagram showing a second embodiment of the present invention.

FIG. 3 which shows a second embodiment of the present invention.

Figure 4:
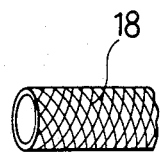
FIG. 4 is an enlarged perspective view showing the mesh shown in FIG. 3.

In the Figure, the same reference numerals are used to designate the same or corresponding elements as those in FIG. 2. The reference numeral 18 designates a mesh provided covering the outer surface of the cylindrical bubbling pipe 13 which is also shown in FIG. 4.

The main operation for measuring and continuously monitoring the absolute value of the density of salts in atmosphere is the same as that of the device of FIG. 2. In this embodiment bubbles generated from the bubbling pipe 13 are minimized by the mesh 18, and therefore, the surface area ratio of the air and the super pure water contacting with each other is increased. Furthermore, the velocity of the air supplied to the bubbling pipe 13 is controlled by the valve 9 and the flow meter 11 to be equal to that of the air flow outside the device. For example, when the device is installed outside, said velocity is made equal to the velocity of the outside air flow, and when the device is installed in a clean room which is ventilated, said velocity is made equal to the velocity of the air flow inside the room. This makes it possible to obtain a stable result regardless of changes of the state of the atmosphere, and it is especially effective for use in a seaside region.

In the above illustrated embodiment, the mesh 18 is provided outside the bubbling pipe 13, but this can be provided inside thereof.

Furthermore, it is, of course, possible to control the quantity of air and the time period for bubbling depending upon the density of salts in atmosphere at the place where the measurement is conducted. The sodium ion analyzer has a measuring range from 0.1ppb to 1,000ppb, and it may be provided with an alarming function to output an alarm signal when the measured result exceeds the upper limit of the measuring range as a countermeasure against a high density of salts in a seaside region.

According to the device of FIG. 3, bubbles are minimized by a mesh provided at the outer surface of the bubbling means, and therefore, the surface area ratio of the air and the super pure water contacting with each other substantially increases. This enhances the accuracy to a great extent in measuring and continuously monitoring the density of salts in atmosphere.

What is claimed is:

1. A device comprising: means for measuring the absolute value of the density of salts in the atmosphere, including, an airtight water tank containing super pure water;

means for supplying super pure water to said airtight water tank;

means for bubbling a predetermined quantity of air from the atmosphere into the predetermined quantity of super pure water, wherein said means for bubbling is provided in said airtight water tank;

means for exhausting the super pure water in said airtight water tank after the bubbling;

sodium ion analyzer means for measuring the density of sodium ions in the exhausted super pure water, wherein said analyzer means has both a material taking inlet and outlet; and background value measuring means for measuring the density of sodium ions in the super pure water at said means for supplying super pure water while bubbling.

2. A device as defined in claim 1, wherein said background value measuring means includes a sodium ion analyzer at the exhausted super pure water and bypass means, originating at said means for supplying super pure water, for supplying super pure water to the material taking inlet of said sodium ion analyzer means.

3. A device as defined in claim 2, wherein said bypass means includes a bypass pipe circumventing said means for bubbling and a valve operatively disposed in said bypass pipe.

4. A device as defined in claim 3, wherein said bypass pipe is located upstream of the flow of the exhausted water relative to said material taking inlet of said sodium ion analyzer means.

5. A device comprising: means for measuring the absolute value of the density of salts in the atmosphere, including,
an airtight water tank containing super pure water;
means for supplying super pure water to said airtight water tank;
means for bubbling a predetermined quantity of air from the atmosphere into the super pure water, wherein said means is provided in said airtight water tank;
means for exhausting the super pure water in said airtight water tank after the bubbling;
sodium ion analyzer means for measuring the density of sodium ions in the exhausted super pure water wherein said analyzer means has both a material taking inlet and outlet;
background value measuring means for measuring the density of sodium ions in the super pure water at said means for supplying super pure water while bubbling; and
means for washing said airtight water tank with super pure water after the super pure water in said airtight water tank is exhausted by said means for exhausting.

6. A device as defined in claim 5, wherein said means for washing is a washing pipe extending from above said airtight water tank to the internal walls of said airtight water tank.

7. A device as defined in claim 6, wherein said washing pipe branches into a plurality of pipes inside said water tank.

8. A device comprising: means for measuring the absolute value of the density of salts in the atmosphere, including,
an airtight water tank containing super pure water;
means for bubbling a predetermined quantity of air from the atmosphere into a predetermined quantity of super pure water in said airtight water tank, wherein said means is provided in said airtight water tank;
a mesh provided at said means for bubbling;
means for supplying the air from the atmosphere to said means for bubbling;
means for exhausting the super pure water in said airtight water tank after bubbling; and
sodium analyzer means for measuring the density of sodium ions in the exhausted super pure water wherein said analyzer means has both a material taking inlet and outlet.

9. A device as defined in claim 8, wherein the air from the atmosphere is supplied to said means for bubbling for a predetermined length of time.

10. A device as defined in claim 8, wherein said means for supplying air to said means for bubbling is at a controlled velocity equal to that of the air flow outside of said device.

11. A device as defined in claim 8, wherein said means for bubbling is an elongated cylindrical pipe having a plurality of openings in the surface thereof.

12. A device as defined in claim 11, wherein said mesh is provided at the outer surface of said elongated cylindrical bubbling pipe.

* * * * *